US011311699B2

(12) United States Patent
Weisz et al.

(10) Patent No.: US 11,311,699 B2
(45) Date of Patent: Apr. 26, 2022

(54) MULTI-DIMENSIONAL NAVIGATION WITHIN A BODY CHAMBER (71) Applicants: Giora Weisz, Tenafly, NJ (US); Idan Tobis, Beth Hashmonai (IL)

(72) Inventors: Giora Weisz, Tenafly, NJ (US); Idan Tobis, Beth Hashmonai (IL)

(*) Notice: Subject to any disclaimer, the term of this patent is extended or adjusted under 35 U.S.C. 154(b) by 0 days.

(21) Appl. No.: 16/624,746

(22) PCT Filed: Jun. 4, 2018

(86) PCT No.: PCT/US2018/035849
§ 371 (c)(1),
(2) Date: Dec. 19, 2019

(87) PCT Pub. No.: WO2019/005428
PCT Pub. Date: Jan. 3, 2019

(65) Prior Publication Data
US 2021/0162177 A1 Jun. 3, 2021

Related U.S. Application Data (60) Provisional application No. 62/527,864, filed on Jun. 30, 2017.

(51) Int. Cl.
*A61M 25/01* (2006.01)
*A61M 25/04* (2006.01)

(52) U.S. Cl.
CPC .... *A61M 25/0147* (2013.01); *A61M 25/0136* (2013.01); *A61M 25/04* (2013.01); *A61M 2205/0266* (2013.01)

(58) Field of Classification Search
CPC .............. A61M 25/04; A61M 25/0147; A61M 25/0136; A61M 2205/0266;
(Continued)

(56) References Cited

U.S. PATENT DOCUMENTS

| 5,324,304 A | 6/1994 | Rasmussen |
| 8,224,416 B2 | 7/2012 | de la Rama et al. |

(Continued)

FOREIGN PATENT DOCUMENTS

| WO | 2014066383 A1 | 5/2014 |
| WO | 2016189391 A2 | 12/2016 |
| WO | 2018035378 A1 | 2/2018 |

OTHER PUBLICATIONS

EPO, Search Report on 18824741.5, pp. 7 (dated Mar. 1, 2021).
(Continued)

*Primary Examiner* — Emily L Schmidt
*Assistant Examiner* — Joshua Parker Reddington
(74) *Attorney, Agent, or Firm* — UltimatEdge IP Law Group, P.C.; Dean G. Stathakis (57) ABSTRACT Systems and methods for directing a device to a target region within a body cavity are provided. One embodiment includes a first catheter having a handle, an expandable cage, and a lumen therethrough, the expandable cage having a plurality of members that expand to engage a wall of the body cavity, a second catheter within the first catheter lumen having a hub at a distal end, and a plurality of pairs of wires secured at a first end within the handle of the first catheter and secured at a second end to the hub of the second catheter, each pair of wires being movable in conjunction with each other by manipulation of the handle so as to move the hub, a first pair of wires movable to move the hub in a first direction and a second pair of wires movable to move the hub in a second direction.

22 Claims, 8 Drawing Sheets

(58) Field of Classification Search
CPC ......... A61F 2002/016; A61F 2002/018; A61B 17/12145; A61B 17/12154; A61B 17/12022; A61B 17/1214; A61B 2017/1205; A61B 17/12122; A61B 17/1217; A61B 17/221; A61B 2017/2212; A61B 2017/2215; A61B 2017/2217; A61B 2017/003; A61B 2017/00318; A61B 2017/00323; A61B 2017/00327; A61B 2017/00336; A61B 2017/00623; A61B 2017/22069

See application file for complete search history.

(56) References Cited

U.S. PATENT DOCUMENTS

| | | | |
|---|---|---|---|
| 8,694,077 B2 | 4/2014 | Kapadia | |
| 9,301,838 B2 | 4/2016 | Kapadia | |
| 9,492,623 B2 | 11/2016 | Kapadia | |
| 2003/0109889 A1* | 6/2003 | Mercereau | A61B 17/221 |
| | | | 606/127 |
| 2008/0249397 A1 | 10/2008 | Kapadia | |
| 2010/0076426 A1 | 3/2010 | de la Rama et al. | |
| 2010/0168737 A1* | 7/2010 | Grunewald | A61B 18/1492 |
| | | | 606/41 |
| 2010/0191232 A1* | 7/2010 | Boveda | A61B 18/14 |
| | | | 606/33 |
| 2013/0110154 A1 | 5/2013 | van der Burg et al. | |
| 2014/0309679 A1 | 10/2014 | Maisano et al. | |
| 2015/0366440 A1 | 12/2015 | Rothe et al. | |
| 2016/0374657 A1 | 12/2016 | Kreidler | |
| 2017/0290595 A1 | 10/2017 | Miles et al. | |

OTHER PUBLICATIONS

WIPO, PCT Form ISA210 International Search Report on PCT/2018/035849, pp. 4 (dated Aug. 3, 2018).
WIPO, PCT Form ISA237 Written Opinion on PCT/2018/035849, pp. 6 (dated Aug. 3, 2018).
WIPO, PCT Form IB373 International Preliminary Report on Patentability on PCT/2018/035849, pp. 6 (dated Jan. 9, 2020).

* cited by examiner

MULTI-DIMENSIONAL NAVIGATION WITHIN A BODY CHAMBER

This application is a national stage entry pursuant to 35 U.S.C. § 371 of International Patent Application Serial No. PCT/US2018/035849, which claims the benefit of priority and filing date of U.S. Provisional Patent Application Ser. No. 62/527,864, filed Jun. 30, 2017, the entire contents of which are incorporated herein by reference.

BACKGROUND present invention relates in general to apparatuses and methods for delivering devices to a target site within a cavity or chamber of the body, such as for example the atria or ventricles of the heart, the gastrointestinal system, the urinary bladder, the lungs or the uterus.

Various pathologies call for the delivery of therapeutic devices, e.g., valve repair or valve replacement devices, to cavities or chambers of the human body. For instance, valve repair often requires specific location of the intra-atrial transseptal puncture and accurate positioning tissue anchors to locations in the left atrium or left ventricle of the heart. Similarly, uterine myomectomy requires accurate positioning of a dissecting device inside the uterus.

Currently, positioning is usually performed by the physician in the following manner: the catheter may be moved manually forward (towards its distal end) or backward (towards its proximal end). See, for example, the prior art schematic catheter C of FIG. 1, where the catheter C comprises a lumen L, and handle H and a flexible distal tip DT. Such exemplary steerable catheter can be manually rotated around its long axis. The steerable flexible tip may be manipulated by a knob in the handle which pulls a pull-wire to bend the flexible tip. The result is three degrees-of freedom manipulation that can best be described as a hybrid between cylindrical and spherical coordinate systems, in which the main coordinates are rho, theta and the z-axis ($\rho$, $\theta$, Z, respectively), with Z being linear movement of the tip along the long axis of the catheter, $\theta$ being rotational movement of the tip around the long axis of the catheter, and $\rho$ being the bending movement of the tip by steering. This is compared to ($\rho$, $\theta$, $\varphi$) in a purely spherical coordinate system, or (r, $\theta$, z) in a purely cylindrical coordinate system.

The usage of this hybrid coordinate system is compromised by complex and tortuous anatomy and is highly non-intuitive for the operator and thus requires a lengthy learning curve. Furthermore, even for highly trained physicians, it is often very difficult to accurately position the tip of the delivery system. A need has arisen for a more intuitive and precise navigation system that will allow the user to accurately and repeatedly navigate inside chambers or cavities in the human body to allow for precision positioning of various therapeutically tools.

Another prior art device is shown in U.S. Publication No. 2014-0309679A1 to Maisano et al., published Oct. 16, 2014. That device relies upon finding a particular tissue site near the fossa ovalis and then targeting a region within the fossa ovalis for puncture therethrough.

SUMMARY

Embodiments of the present invention address the need for more intuitive steering by providing more accurate positioning of a therapeutic or diagnostic device on the surface of a chamber or cavity of the human body. In some embodiments, the apparatus comprises a catheter, an expandable cage designed to expand to the full extent of the target chamber (or cavity), and a plurality of pairs of wires that are used to linearly move a hub on one surface of the chamber in a cartesian (x, y, z) or semi-cartesian (x, y, $\theta$) manner, which is more intuitive and easier to learn and practice than traditional steering catheters. The cage also provides both a frame of reference for the anatomy, as well as means of providing counter force, which is beneficial for many types of procedures.

In one embodiment, a system is provided for directing a device to a target region within a cavity of a body, where the system comprises (1) a first catheter comprising a handle at a proximate end, an expandable cage at a distal end, and a lumen therebetween, (2) an outer sheath axially movable to alternatively cover and expose the expandable cage to permit the expandable cage to move from a collapsed delivery mode to an expanded deployed mode, the expandable cage comprising a plurality of members that expand to engage a wall of the body cavity to stabilize the cage within the cavity, the cage being rotatable within the cavity when the handle of the first catheter is rotated, (3) a second catheter positioned within the lumen of the first catheter, the second catheter comprising a proximal end that passes through the handle of the first catheter and a distal end that passes through a hub, the second catheter comprising a lumen therethrough, the second catheter being axially and rotationally movable within the lumen of the first catheter in association with axial and rotational movement of the expandable cage, and (4) a plurality of pairs of wires, each wire having a first end secured within the handle of the first catheter and a second opposite end secured at the hub of the second catheter, each pair of wires being movable in conjunction with each other by manipulation of the handle so as to move the hub, and thereby the distal end of the second catheter, a first pair of wires movable to move the hub in a first direction and a second pair of wires movable to move the hub in a second direction, whereby, through manipulation of the handle and wires, the distal end of the second catheter may be rotated within the cavity while moved in the first and second direction.

In one embodiment, a first member of the expandable cage comprises a generally annular member defining a first plane, and wherein a second member of the expandable cage comprises a generally semi-annular member defining a second plane generally orthogonal to the first plane. In one embodiment, the handle comprises a first static portion and a second movable portion, the second movable portion configured to manipulate the plurality of pairs of wires so as to cause lateral movement of the hub and distal end of second catheter in first and second directions. In one embodiment, the members of the expandable cage comprise shape-memory material. In one embodiment, the lumen of the second catheter is configured so as to permit the passage therethrough of a therapeutic or diagnostic device for delivery to the target region to where the hub and distal end of the second catheter have been directed.

In one application, a method is provided for directing a device to a target region within a cavity of a body, where the method comprises (A) delivering a navigation system to the body cavity, the system comprising: (1) a first catheter comprising (a) a handle at a proximate end, an expandable cage at a distal end, and a lumen therebetween, and (b) an outer sheath axially movable to alternatively cover and expose the expandable cage to permit the expandable cage to move from a collapsed delivery mode to an expanded deployed mode, the expandable cage comprising a plurality of members that expand to engage a wall of the body cavity to stabilize the cage within the cavity while being rotatable within the cavity as desired, and (2) a second catheter positioned within the lumen of the first catheter, the second catheter having a proximal end and that passes through the handle of the first catheter and a distal end that passes through a hub, the second catheter comprising a lumen therethrough, the second catheter being axially and rotationally movable within the lumen of the first catheter in association with axial and rotational movement of the expandable cage; and (B) manipulating a plurality of pairs of wires to direct placement of the hub and distal end of the second catheter to a target region, the plurality of wires secured at a first end within the handle of the first catheter and secured at a second end to the hub of the second catheter, each pair of wires being movable in conjunction with each other by manipulation of the handle so as to move the hub, and thereby the distal end of the second catheter, a first pair of wires movable to move the hub in a first direction and a second pair of wires movable to move the hub in a second direction, whereby, through manipulation of the handle and wires, the distal end of the second catheter may be rotated within the cavity while moved in the first and second direction.

In one application, a first member of the expandable cage comprises a generally annular member defining a first plane, and wherein a second member of the expandable cage comprises a generally semi-annular member defining a second plane generally orthogonal to the first plane. In one application, the handle comprises a first static portion and a second movable portion, the second movable portion configured to manipulate the plurality of pairs of wires so as to cause lateral movement of the hub and distal end of second catheter in first and second directions. In one application, the members of the expandable cage comprise shape-memory material. In one application, the method further comprises directing through the lumen of the second catheter a therapeutic or diagnostic device for delivery to the target region to where the hub and distal end of the second catheter have been directed.

BRIEF DESCRIPTION OF THE FIGURES

The aforementioned objects and advantages of the present invention, as well as additional objects and advantages thereof, will be more fully understood hereinafter as a result of a detailed description of a preferred embodiment when taken in conjunction with the following drawings in which.

DETAILED DESCRIPTION OF CERTAIN EMBODIMENTS

Figure 1:
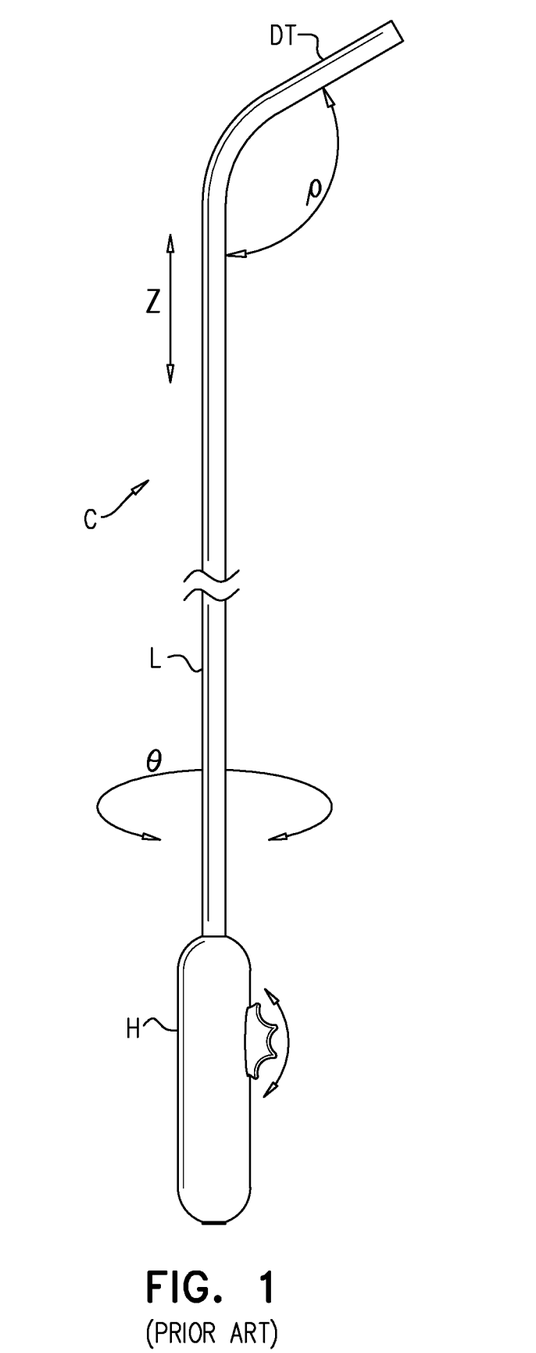
FIG. 1 shows a perspective elevational view of a prior art steering catheter.

By way of example, and referring to FIG. 1, one embodiment of the prior art steering catheter comprises a catheter C with handle H and lumen L, where the distal tip DT of the lumen is steerable in three degrees of movement, including (a) moving the distal tip of the catheter at an angle theta θ by turning the handle clockwise or counterclockwise, (b) moving the distal tip axially along the z-axis by pushing the handle distally or proximally, (c) steering the distal tip laterally at an angle rho by moving a control knob on the handle to reach a desired target region.

Figure 2A:
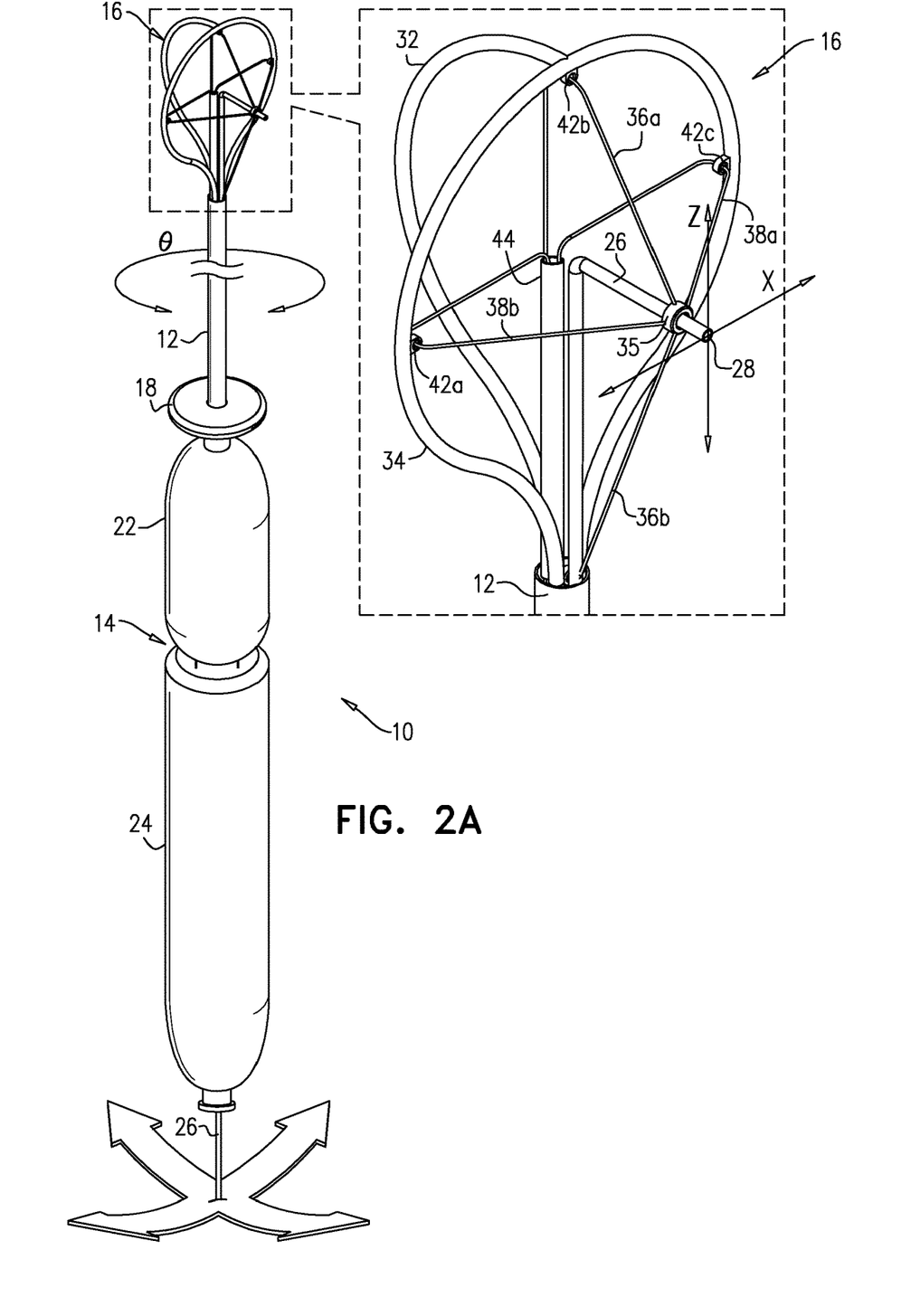
FIG. 2A shows a perspective view of one embodiment of the present invention.

Embodiments of the present system provide a better system for reaching a target region with a therapeutic or diagnostic device. Referring to FIG. 2A, one embodiment of the present system can be described. In that regard, embodiment 10 comprises, in one example, a catheter 11, an outer sheath 12, a handle 14, an expandable cage 16, and a member 18 for advancing distally or pulling back proximally the outer sheath 12 to respectively cover and expose the expandable cage 16. The expandable cage 16 may be made of shape-memory material, such as Nitinol, and can be collapsed for delivery within outer sheath 12 of embodiment 10, or expanded as shown at the distal end of the outer sheath 12. In one embodiment, the handle 14 comprises a first portion 22, which remains fixed, and a second portion 24, which can be manipulated somewhat like a joy stick, as described below. Within outer sheath 12 a second inner sheath 26 is provided within catheter 11, which second inner sheath 26 extends from a proximal end through the handle and extends from a distal end through the expandable cage 16, as further described below.

In one embodiment, the expandable cage 16 comprises a first member 32 and a second member 34, each defining a plane, with one plane being generally orthogonal to the other plane. In one embodiment, the first member 32 is generally semi-annular in shape, while the second member 34 is generally annular in shape, with the configuration being intended to expand to occupy a cavity within a body (not shown). The expandable cage, however, may comprise any number of configurations intended to expand to occupy a body cavity to provide distal stabilization.

At one side of the expandable cage 16, preferably opposite the first member 32 of the cage in the example embodiment shown, is the distal portion of the second inner catheter 26 having a distal end 28 penetrating a hub 35 connected to the cage 16 via a plurality of pairs of wires. Specifically, in one embodiment, hub 35 is connected to first pair of wires 36 and second pair of wires 38. A first end of each wire (36a, 36b, 38a, 38b) of each pair is connected to hub 35, while a second opposite end of each wire is connected to the second portion 24 of handle 14, as described more fully below. Wires 38a, 38b and 36a are fed through rings 42c, 42a and 42b, respectively, where the rings 42a-c are mounted to the second member 34 of cage 16. Those three wires are then directed through a sheath 44 provided within outer sheath 12 and catheter 11. Fourth wire 36b is provided directly into catheter 11 and directed to second portion 24 of handle 14.

Each pair of wires 36, 38 moves in unison such that while one wire of each pair is pulled proximally, the other wire of each pair is pulled distally, allowing movement of the hub 35 and distal end 28 of second catheter 26 back and forth in either an X or Z axis. First pair of wires 36 can be manipulated to move hub 35 and distal end 28 back and forth in the Z axis, while second pair of wires 38 can be manipulated to move hub 35 and distal end 28 back and forth in the X axis. An analogy would be moving the hub 35 north and south in one direction, and east and west in the other direction. With the addition of the fact that cage 16 can be rotated within a body cavity at any angle theta θ, the result is that hub 35 and distal end 28 can be moved controllably in multiple degrees of freedom, 3 in this example, allowing greater accuracy in reaching a target region of the cavity. It should be noted that additional pairs of wires may be provided if so desired to add multiple degrees of freedom.

Figure 2B:
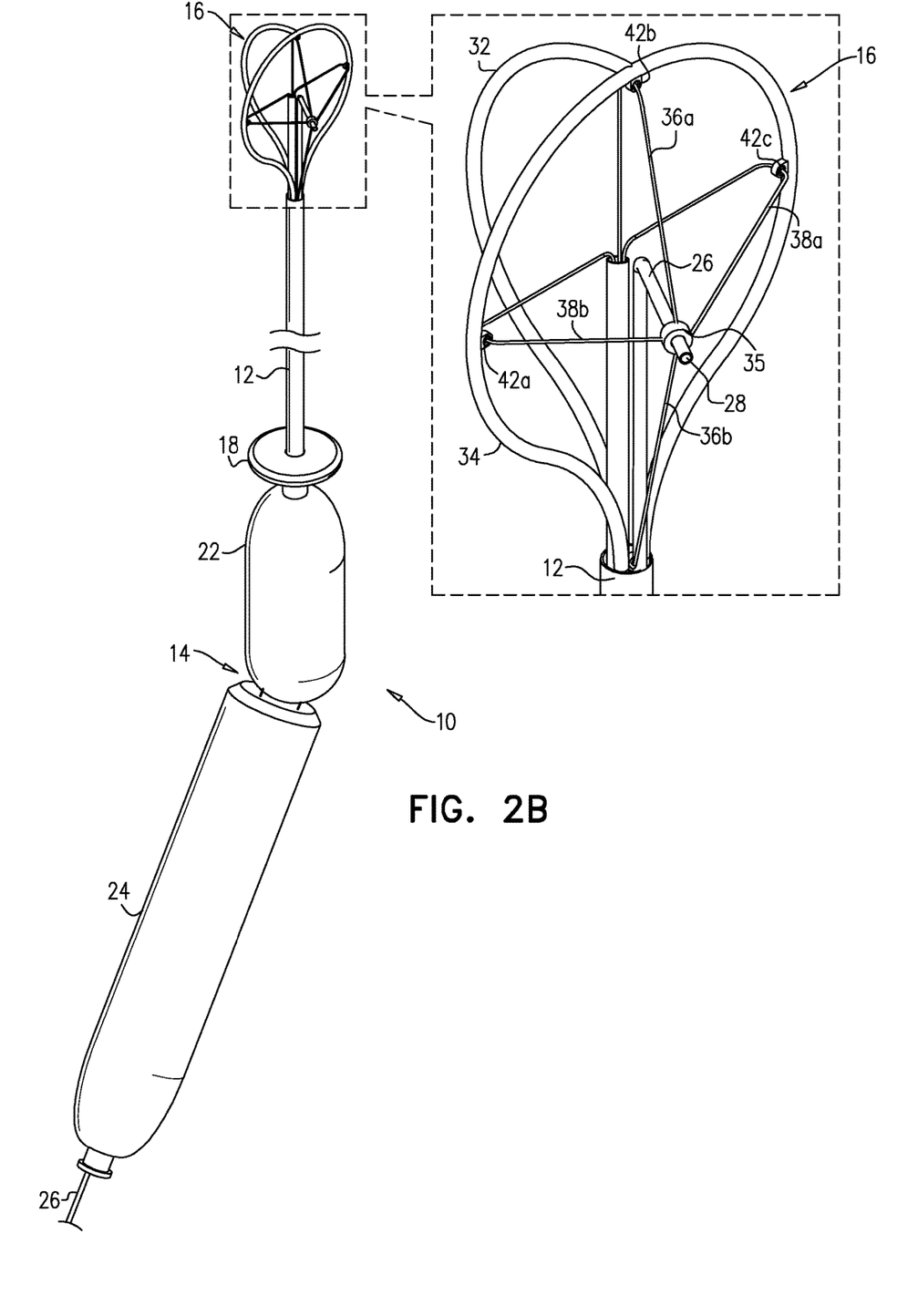
FIGS. 2B-2E show the embodiment of FIG. 2A with the second portion of the handle being manipulated to show the degrees of freedom of movement of the system.
Figure 2C:
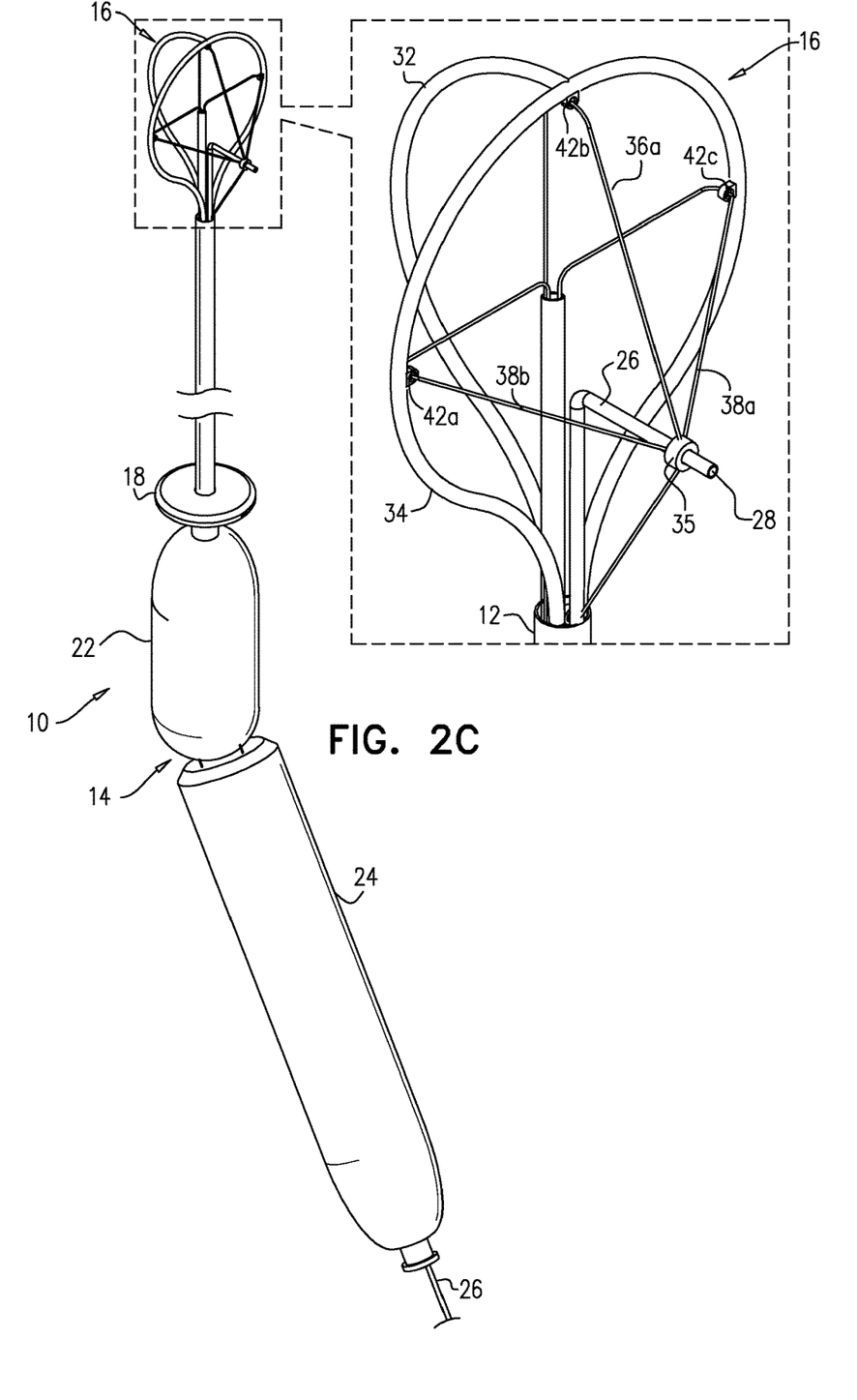
Figure 2D:
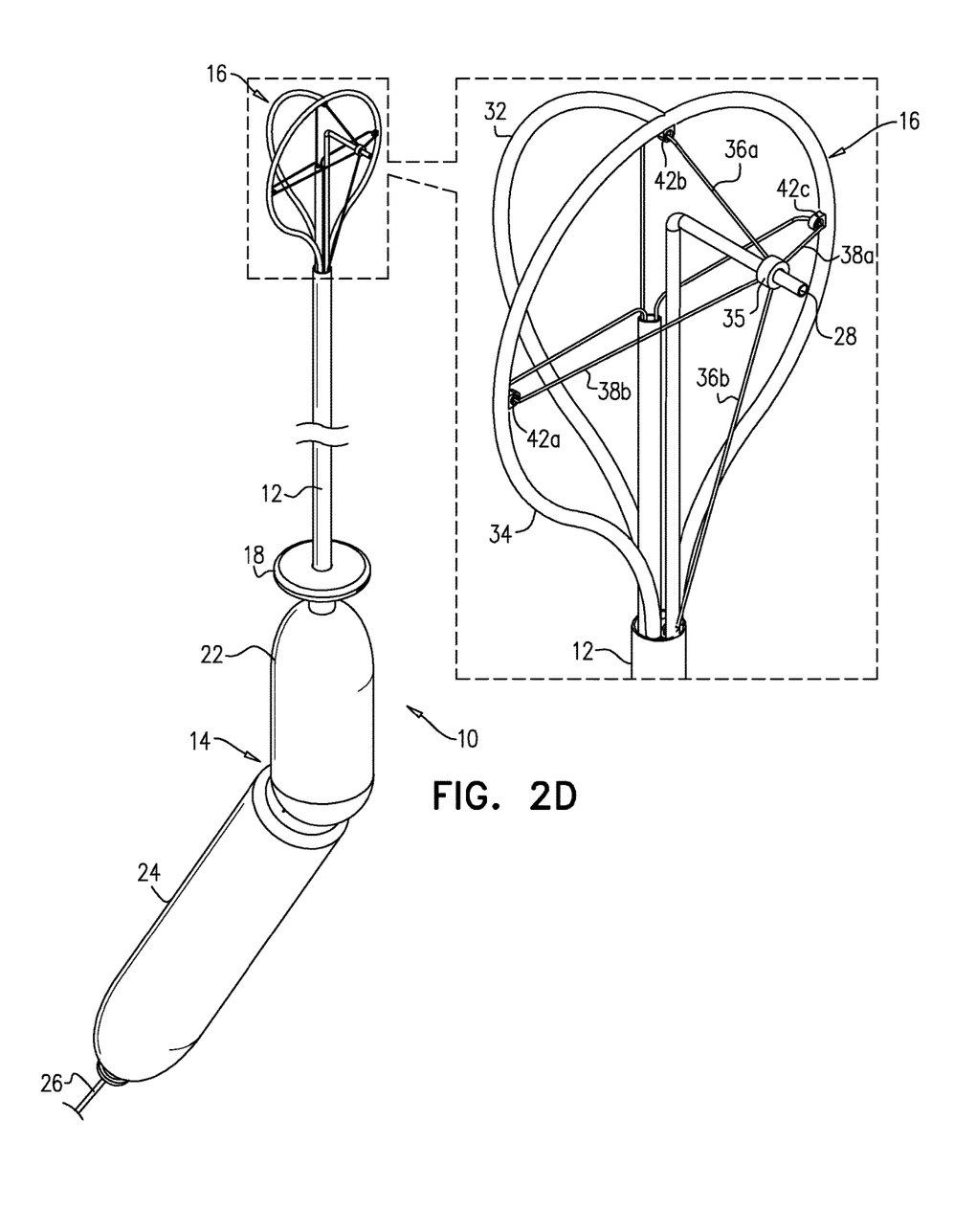
Figure 2E:
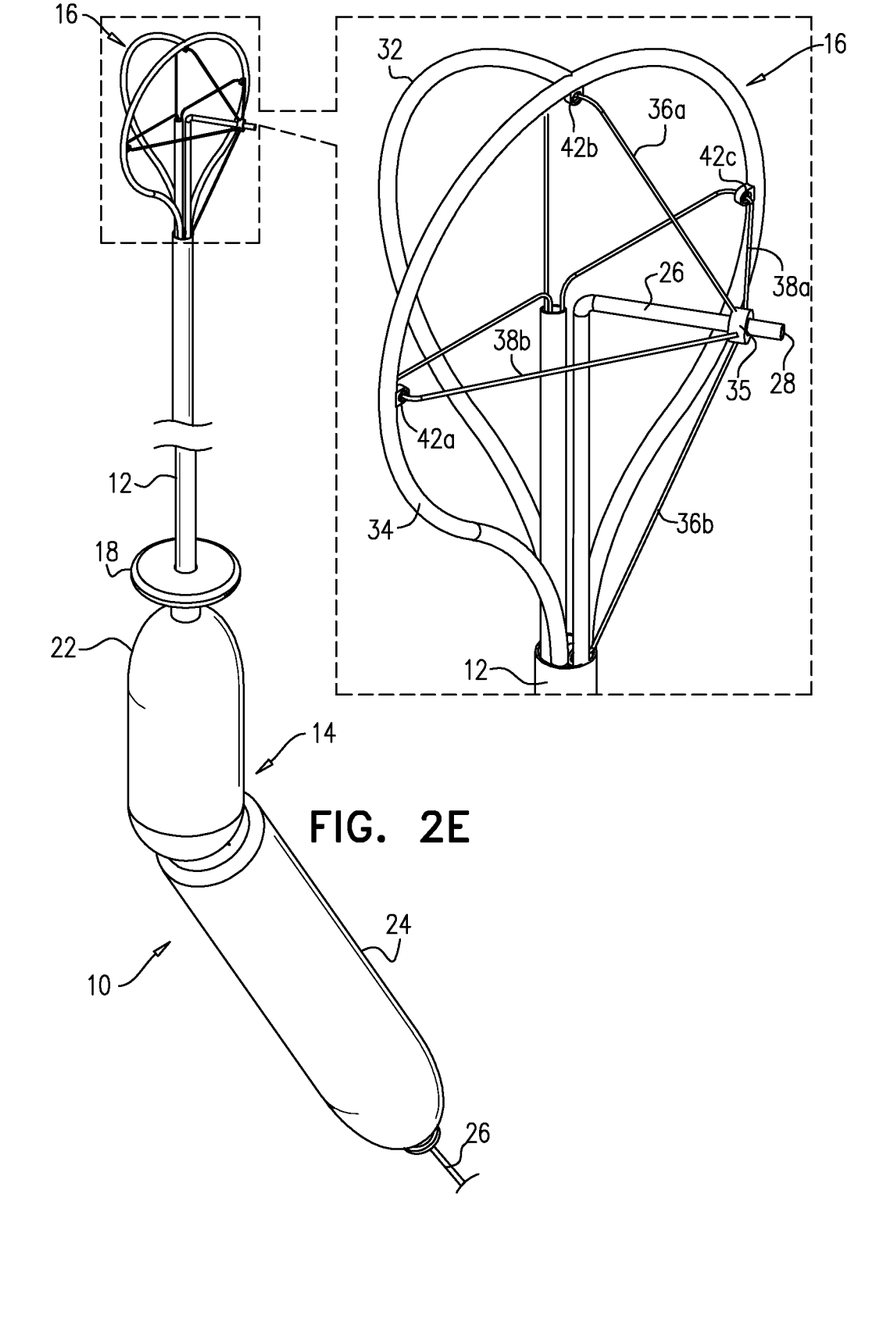

Referring to FIGS. 2B-2E, one embodiment of the present invention can be seen in one of four different positions, where second portion 24 of handle 16 is manipulated in four different directions, leading to the concomitant movement of hub 35 and distal end 28 responsively. In FIG. 2B, the movement of second portion 24 of handle 14 in the direction shown translates to movement of the hub 35 and distal end 28 in a first direction along the X-axis, as shown in the close up view of FIG. 2B. In FIG. 2C, movement of second portion 24 of handle 14 in the direction shown translates to movement of the hub 35 and distal end 28 in a first direction along the Z-axis, as shown in the close up view of FIG. 2B. In FIG. 2D, movement of second portion 24 of handle 14 in the direction shown translates to movement of the hub 35 and distal end 28 in an opposite direction along the Z-axis. In FIG. 2E, movement of second portion 24 of handle 14 in the direction shown translates to movement of the hub 35 and distal end 28 in an opposite direction along the X-axis.

Figure 3:
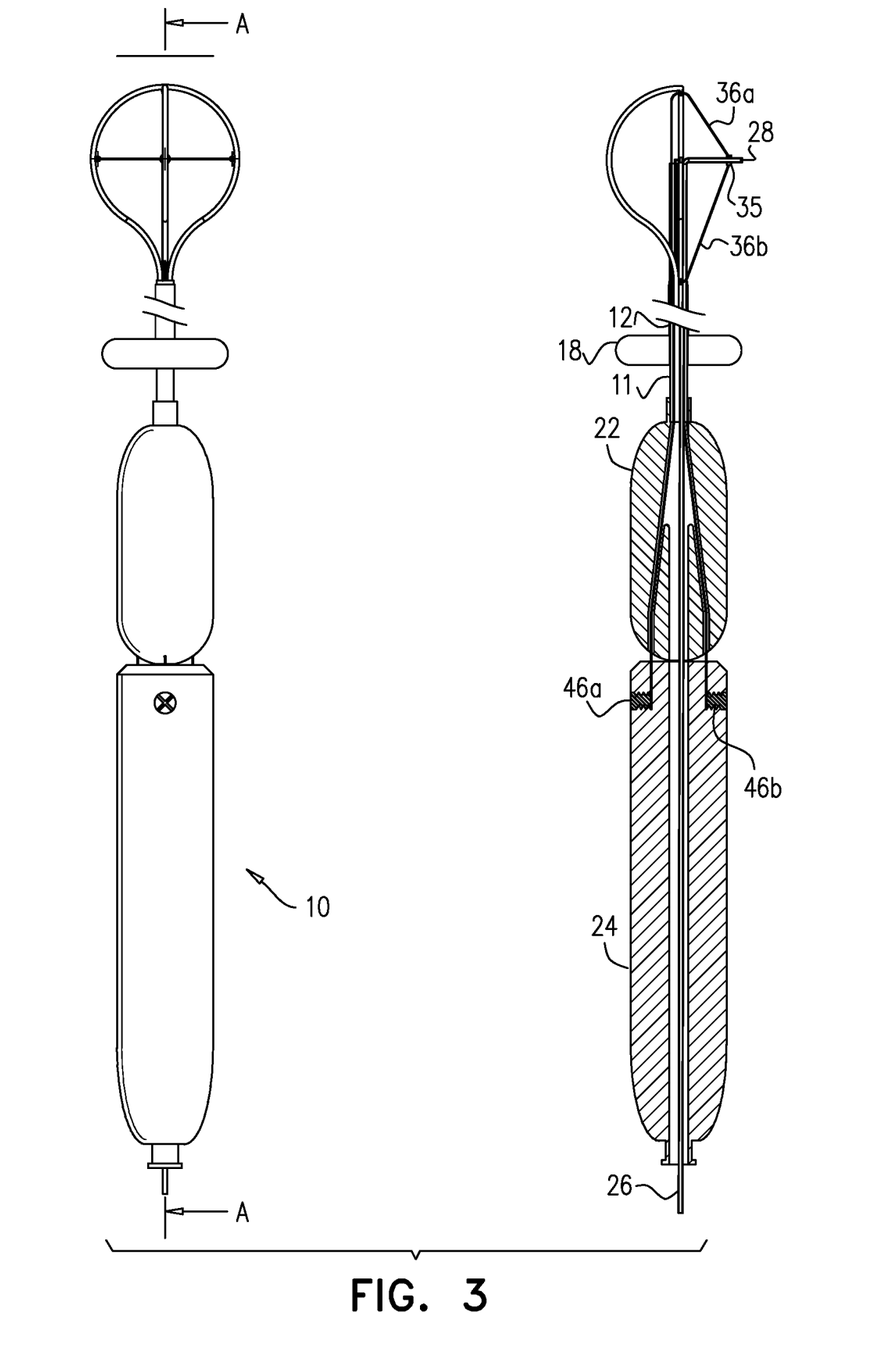
FIG. 3 shows an elevational view of the embodiment of FIG. 2A on the left and a cross-sectional view on the right taken along section A-A.
Figure 4:
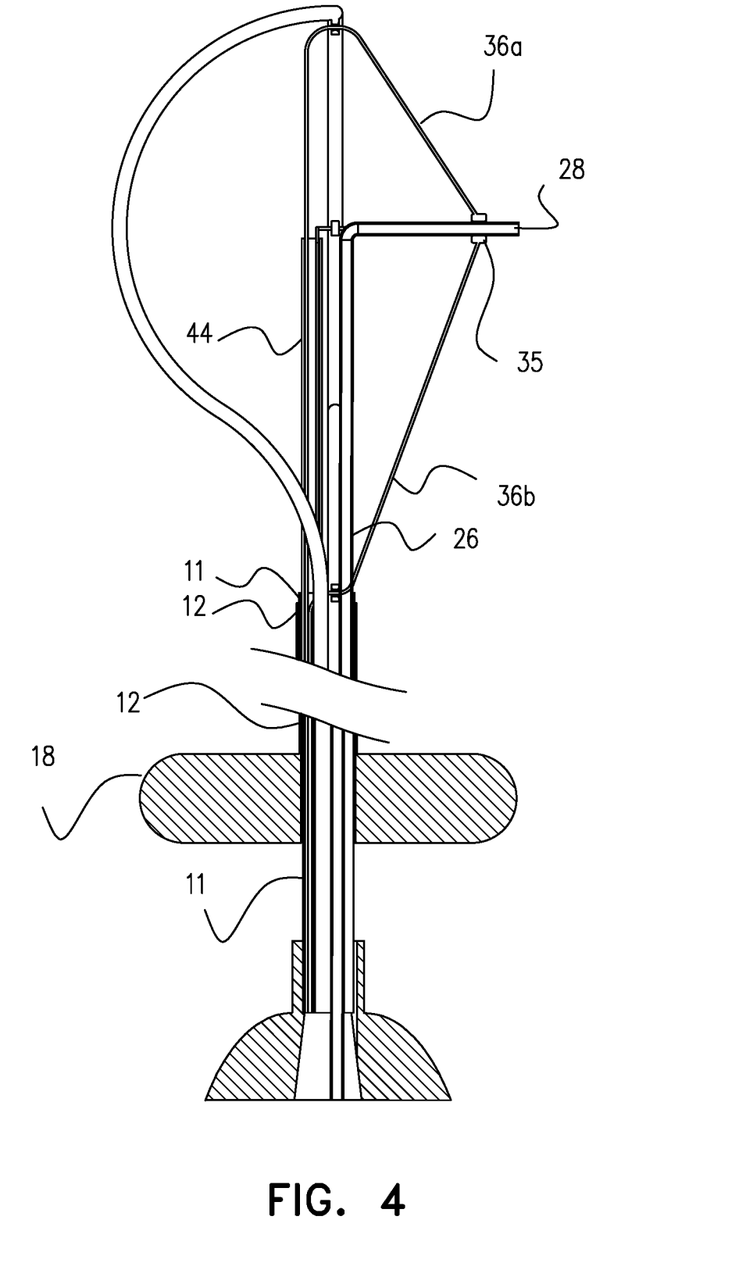
FIG. 4 shows a close up cross section of the embodiment of FIG. 3.

Referring to FIGS. 3 and 4, it can be seen that first pair or wires 36a, 36b travel through outer sheath 12 and catheter 11, through first portion 22 of handle 16 and are then secured within the second portion 24 of handle 16, where the proximal ends of the first pair of wires are connected to the second portion 24 at securing means 46a and 46b, respectively. The securing means 46a, 46b can be one of any type of device sufficient to secure the end of the wire to the handle. The second pair of wires are also connected to the second portion 24 at a second set of securing means (not shown) that are orthogonal to securing means 46a, 46b.

As appreciated from the left view of FIG. 3, when the second portion 24 of handle 16 is moved to the left and to the right (in the vertical plane of the paper), the hub 35 and distal end 28 move responsively back and forth in the a first axis. When the second portion 24 of handle 16 is moved outwardly and inwardly (in the vertical plane of the paper), the hub 35 and distal end 28 move responsively back and forth in the second direction by manipulating pair of wires 38a, 38b (not shown in the cross section of FIG. 3).

With embodiments of the present system, a therapeutic or diagnostic device can be inserted through the inner sheath 26 so that a distal end of the device can be directed to the target region by movement of the hub 35 and distal end 28 of the inner sheath 26. Embodiments of the present invention permit a more accurate and intuitive targeting of the desired region to which the therapeutic or diagnostic device is intended to reach.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A system for directing a device to a target region within a cavity of a body, the system comprising:
    a first catheter comprising a handle at a proximate end, an expandable stabilizing cage configured to extend from a port at a distal end, and a lumen therebetween;
    an outer sheath having an outer sheath port at an outer sheath distal end, the outer sheath covering the first catheter and axially movable to alternatively cover and expose the expandable stabilizing cage to permit the expandable stabilizing cage to move from a collapsed delivery mode to an expanded deployed mode with the expandable stabilizing cage configured to extend from both the port and the outer sheath port, the expandable stabilizing cage comprising a first member arranged in a first plane and a second member arranged in a second plane intersecting the first plane that are configured to expand to engage a wall of the cavity of the body in the deployed mode to stabilize the expandable stabilizing cage within the cavity, the expandable stabilizing cage being configured to be rotatable within the cavity of the body when the handle is rotated;
    a second catheter positioned within the lumen of the first catheter, the second catheter comprising a second catheter proximal end that passes through the handle and a second catheter distal end configured to extend from both the port and the outer sheath port, the second catheter comprising a second catheter lumen therethrough, the second catheter being axially and rotationally movable within the lumen of the first catheter in association with axial and rotational movement of the expandable cage; and
    a plurality of second catheter control wires, each of the plurality of second catheter control wires having a first end secured within the handle and a second opposite end coupled with the second catheter near the second catheter distal end, with at least one of the plurality of second catheter control wires being slidably coupled to a portion of the expandable stabilizing cage between the first end and the second opposite end of the least one of the plurality of second catheter control wires, each of the plurality of second catheter control wires are configured to be movable so as to move the second catheter distal end relative to the expandable stabilizing cage to direct the second catheter distal end to the target region to thereafter deliver the device to the target region through the second catheter lumen.

2. The system of claim 1, wherein the first member of the expandable stabilizing cage comprises a generally annular member defining the first plane, and wherein the second member of the expandable stabilizing cage comprises a generally semi-annular member defining the second plane generally orthogonal to the first plane.

3. The system of claim 1, wherein the handle comprises a first static portion and a second movable portion, the second movable portion being movable relative to the first static portion, each of the plurality of second catheter control wires passing through the first static portion and the first end of each of the plurality of second catheter control wires being secured to the second movable portion, the second movable portion configured to manipulate the plurality of second catheter control wires so as to cause lateral movement of the second catheter distal end.

4. The system of claim 1, wherein the expandable stabilizing cage comprises a shape-memory material.

5. The system of claim 1, further comprising a hub coupled to the second catheter distal end, wherein the second opposite end of each of the plurality of second catheter control wires are coupled to the second catheter distal end through the hub.

6. The system of claim 1, wherein at least one of the plurality of second catheter control wires pass through a ring mounted to the expandable stabilizing cage.

7. The system of claim 1, wherein the plurality of second catheter control wires comprises a first control wire and a second control wire, wherein:
    a first ring is mounted to a first portion of the expandable stabilizing cage with the first control wire passing through the first ring; and a second ring is mounted to a second portion of the expandable stabilizing cage opposing the first portion cage with the second control wire passing through the second ring;

wherein the pulling of the first wire causes the second catheter distal end to move in a first direction and pulling of the second wire causes the second catheter distal end to move in a second direction substantially opposite the first direction.

8. The system of claim 7, wherein the plurality of second catheter control wires further comprises a third control wire and a fourth control wire, wherein:

a third ring is mounted to a third portion of the expandable stabilizing cage with the third control wire passing through the third ring;

wherein pulling of the third wire causes the second catheter distal end to move in a third direction substantially orthogonal the first direction and the second direction and pulling of the fourth control wire causes the second catheter distal end to move in a fourth direction substantially opposite the first direction.

9. A method for directing a device to a target region within a cavity of a body, the method comprising; delivering a navigation system to the body cavity, the system comprising: (1) a first catheter comprising (a) a handle at a proximate end, an expandable stabilizing cage configured to extend from a port at a distal end, and a lumen therebetween, and (b) an outer sheath having an outer sheath port at an outer sheath distal end, the outer sheath covering the first catheter and axially movable to alternatively cover and expose the expandable stabilizing cage to permit the expandable stabilizing cage to move from a collapsed delivery mode to an expanded deployed mode with the expandable stabilizing cage configured to extend from both the port and the outer sheath port, the expandable stabilizing cage comprising a first member arranged in a first plane and a second member arranged in a second plane intersecting the first plane that are configured to expand to engage a wall of the cavity of the body in the deployed mode to stabilize the expandable stabilizing cage within the cavity while being rotatable within the cavity when the handle is rotated, and (2) a second catheter positioned within the lumen of the first catheter, the second catheter having a second catheter proximal end and that passes through the handle and a second catheter distal end configured to extend from both the port and the outer sheath port, the second catheter comprising a second catheter lumen therethrough, the second catheter being axially and rotationally movable within the lumen of the first catheter in association with axial and rotational movement of the expandable cage; and manipulating a plurality of second catheter control wires to direct placement of the second catheter distal end of the second catheter to the target region, the plurality of second catheter control wires secured at a first end within the handle and coupled with the second catheter distal end with at least one of the plurality of second catheter control wires being slidably coupled to a portion of the expandable stabilizing cage between the first end and the second opposite end of the least one of the plurality of second catheter control wires, each of the plurality of second catheter control wires are configured to be moveable so as to move the second catheter distal end relative to the expandable stabilizing cage to direct the second catheter distal end to the target region to thereafter deliver the device to the target region through the second catheter lumen.

10. The method of claim 9, wherein the first member of the expandable stabilizing cage comprises a generally annular member defining the first plane, and wherein the second member of the expandable stabilizing cage comprises a generally semi-annular member defining the second plane generally orthogonal to the first plane.

11. The method of claim 9, wherein the handle comprises a first static portion and a second movable portion, the second movable portion being movable relative to the first static portion, each of the plurality of second catheter control wires passing through the first static portion and the first end of each of the plurality of second catheter control wires being secured to the second movable portion, the second movable portion configured to manipulate the plurality of second catheter control wires so as to cause lateral movement of the second catheter distal end.

12. The method of claim 9, wherein the expandable stabilizing cage comprises a shape-memory material.

13. The method of claim 9, further comprising a hub coupled to the second catheter distal end, wherein the second opposite end of each of the plurality of second catheter control wires are coupled to the second catheter distal end through the hub.

14. The method of claim 9, wherein at least one of the plurality of second catheter control wires pass through a ring mounted to the expandable stabilizing cage.

15. The method of claim 9, wherein the plurality of second catheter control wires comprises a first control wire and a second control wire, wherein:

a first ring is mounted to a first portion of the expandable stabilizing cage with the first control wire passing through the first ring; and a second ring is mounted to a second portion of the expandable stabilizing cage opposing the first portion cage with the second control wire passing through the second ring;

wherein the pulling of the first wire causes the second catheter distal end to move in a first direction and pulling of the second wire causes the second catheter distal end to move in a second direction substantially opposite the first direction.

16. The method of claim 15, wherein the plurality of second catheter control wires further comprises a third control wire and a fourth control wire, wherein:

a third ring is mounted to a third portion of the expandable stabilizing cage with the third control wire passing through the third ring;

wherein pulling of the third wire causes the second catheter distal end to move in a third direction substantially orthogonal the first direction and the second direction and pulling of the fourth control wire causes the second catheter distal end to move in a fourth direction substantially opposite the first direction.

17. A system for directing a device to a target region within a cavity of a body, the system comprising: a handle; a first catheter comprising a proximal end, a distal end with a port, and a lumen therebetween, the first catheter extending from the handle; an expandable stabilizing cage configured to extend from the port at the distal end of the first catheter, the expandable stabilizing cage comprising a first member arranged in a first plane and a second member arranged in a second plane intersecting the first plane that are configured to expand to engage a wall of the cavity of the body in a deployed mode to stabilize the expandable stabilizing cage within the cavity, the expandable stabilizing cage being configured to be rotatable within the cavity of the body when the handle is rotated; a second catheter positioned within the lumen of the first catheter, the second catheter comprising a second catheter proximal end and a second catheter distal end configured to extend from the port, the second catheter comprising a second catheter lumen therethrough, the second catheter being axially and rotationally movable within the lumen of the first catheter; and a plurality of second catheter control wires, each of the plurality of second catheter control wires having a first end secured within the handle and a second opposite end coupled with the second catheter near the second catheter distal end, with at least one of the plurality of second catheter control wires being slidably coupled to a respective portion the expandable stabilizing cage between the first end and the second opposite end of the at least one of the plurality of second catheter control wires, each of the plurality of second catheter control wires are configured to be movable so as to move the second catheter distal end relative to the expandable stabilizing cage to direct the second catheter distal end to the target region to thereafter deliver the device to the target region through the second catheter lumen.

18. The system of claim 17, further comprising an outer sheath having an outer sheath port at an outer sheath distal end, the outer sheath covering the first catheter and axially movable to alternatively cover and expose the expandable stabilizing cage to permit the expandable stabilizing cage to move from a collapsed delivery mode to the deployed mode with the expandable stabilizing cage configured to extend from both the port and the outer sheath port.

19. The system of claim 17, further comprising a hub coupled to the second catheter distal end, wherein the second opposite end of each of the plurality of second catheter control wires are coupled to the second catheter distal end through the hub.

20. The system of claim 17, wherein at least one of the plurality of second catheter control wires pass through a ring mounted to the expandable stabilizing cage.

21. The system of claim 17, wherein the plurality of second catheter control wires comprises a first control wire and a second control wire, wherein:
   a first ring is mounted to a first portion of the expandable stabilizing cage with the first control wire passing through the first ring; and
   a second ring is mounted to a second portion of the expandable stabilizing cage opposing the first portion cage with the second control wire passing through the second ring;
   wherein the pulling of the first wire causes the second catheter distal end to move in a first direction and pulling of the second wire causes the second catheter distal end to move in a second direction substantially opposite the first direction.

22. The system of claim 21, wherein the plurality of second catheter control wires further comprises a third control wire and a fourth control wire, wherein:
   a third ring is mounted to a third portion of the expandable stabilizing cage with the third control wire passing through the third ring;
   wherein pulling of the third wire causes the second catheter distal end to move in a third direction substantially orthogonal the first direction and the second direction and pulling of the fourth control wire causes the second catheter distal end to move in a fourth direction substantially opposite the first direction.

\* \* \* \* \*